United States Patent
Hagene et al.

(10) Patent No.: US 6,931,149 B2
(45) Date of Patent: Aug. 16, 2005

(54) PIPELINE INTERNAL INSPECTION DEVICE AND METHOD

(75) Inventors: Jon Kristian Hagene, Dilling (NO); Karl Henrik Haugholt, Oslo (NO); Håvard Tørring, Blystadlia (NO); Kjartan Vartdal, Haugesund (NO)

(73) Assignee: Norsk Elektro Optikk A/S, Skarer (NO)

( * ) Notice: Subject to any disclaimer, the term of this patent is extended or adjusted under 35 U.S.C. 154(b) by 642 days.

(21) Appl. No.: 10/125,515

(22) Filed: Apr. 19, 2002

(65) Prior Publication Data

US 2003/0198374 A1 Oct. 23, 2003

(51) Int. Cl.[7] .................................................. G06K 9/00
(52) U.S. Cl. ................................................... 382/141
(58) Field of Search .............................. 382/141, 143, 382/152, 153; 348/56, 92, 125, 127, 129; 451/151; 356/241.1; 378/89

(56) References Cited

U.S. PATENT DOCUMENTS

| 4,722,001 A | 1/1988 | Rohrich et al. |
| 4,967,092 A | 10/1990 | Fraignier et al. |
| 5,195,117 A * | 3/1993 | Ong ............................. 378/89 |
| 6,264,537 B1 * | 7/2001 | Penza ........................... 451/51 |
| 2004/0021858 A1 * | 2/2004 | Shima et al. ............. 356/241.1 |

FOREIGN PATENT DOCUMENTS

| DE | 196 51 433 | 12/1997 |
| JP | 01-54235 | 3/1989 |
| JP | 1-242516 | 4/1991 |
| JP | 05-149885 | 6/1993 |
| NO | 954881 | 6/1997 |
| WO | WO 83/00738 | 3/1983 |
| WO | WO 95/03526 | 2/1995 |

OTHER PUBLICATIONS

A.E. Crouch, "In–Line Inspection of Natural Gas Pipelines," Topical Report GRI 91–0365 of Gas Research Institute, 1993, Chicago, IL, pp. ii–49 with Appendices A and B.

J.B. Nestleroth et al., "Magnetic Flux Leakage (MLF) Technology for Natural Gas Pipeline Inspection," The Gas Research Institute, 1999, pp. 1–37.

* cited by examiner

Primary Examiner—Vikkram Bali
(74) Attorney, Agent, or Firm—Young & Thompson

(57) ABSTRACT

Apparatus and method for optical inspection of a pipeline (2) for transporting fluid (3) by internal surveying. Light source means (4) are adapted to form one or more beams of light (5) illuminating a line (L) of a surface part (9) of said pipeline (2). Optical receiving means (6) are positioned outside a plane formed by said beams (5) and arranged to have in its field of view (7) the line (L) formed on the internal wall of the pipeline (2) by the beam (5). The receiving means (6) are adapted to form a two-dimensional indexed images ($20_k$) each comprising intensity data for a predetermined number of pixels in each of a predetermined number of lines (M) of said image (20). A data processing unit (100) including an image analyzer module (110) is adapted for extracting a depth profile of said surface (9).

23 Claims, 13 Drawing Sheets

The field of view of 4 of 8 cameras are shown

PIPELINE INTERNAL INSPECTION DEVICE AND METHOD

BACKGROUND OF THE INVENTION

The invention relates to a device for internal inspection of pipelines for petroleum fluid transport, particularly gas or multiphase transport.

FIELD OF THE INVENTION

More specifically, the invention relates to the topic of what is called traditionally a Pipeline Internal Gauge device or PIG device, which may be inserted and run along by the fluid pressure, for inspecting the inner side of the pipe wall for defects of several kinds, e.g. corrosion, deposits, erosion, or mechanical failure.

Natural gas pipelines are built world wide to distribute natural gas from gas fields to end users either through offshore or land pipelines. The gas pressure typically is in the range from 50 to 160 bars, but some systems are designed for pressures up to 200 bars and possibly above. Pipelines are expensive and are often designed and built to last at least as long as the expected lifetime of the source. Pipeline design lifetimes in the range from 40 to 70 years are common. Most pipelines are made from a relatively standard steel alloy that might corrode.

The risk of corrosion combined with the long design lifetime of the pipeline makes inspection a necessity. In the long term perspective a wall thickness reduction as a result of corrosion is a major threat. In a short term perspective other aspects such as beginning corrosion, damages to the internal coating and undesired results of operational events are also of interest, and should be monitored.

A wall thickness reduction will entail a reduced pressure rating for the pipeline and as a consequence a reduced gas production and an economic loss may occur. If the wall thickness is not monitored, corrosion could cause leaks with associated risk of pollution, and in even more unfortunate cases also fire and/or explosions could occur.

DESCRIPTION OF RELATED ART

Pipeline inspection is described in a topical report, CRI 91-0365, *"IN-LINE INSPECTION OF NATURAL GAS PIPELINES"*, prepared by Southwest Research Institute, San Antonio, Tex., for GAS RESEARCH INSTITUTE, Chicago, Ill. May 1993.

A report entitled *"Magnetic Flux Leakage (MFL) Technology For Natural Gas Pipeline inspection"* has been made by J. B. Nestleroth and T. A. Bubenik, Battelle, for The Gas Research Institute in February 1999.

Norwegian patent application NO 1995.4881, filed by Norsk Elektro Optikk A/S, describes spectral imaging and identification of surface details in oil and gas pipelines, such as corrosion, fluid film and mechanical damage.

Japanese patent application JP 05-149885 uses a light source forming a narrow fan-shaped light beam directed towards and forming a light line on the inner wall of a pipeline. This line is imaged by a camera and is processed by a detection controller. Use of two light sources and colour imaging is also described.

JP 01-54235 describes a pig for pipeline inspection, the pig comprising a light source illuminating the inner pipeline surface via an optical fibre, and a camera observing the illuminated spot position and diameter to determine the size and depth of wall cavity defects in the inner pipeline surface.

Common internal inspection techniques are based on ultra sound testing and Magnetic Flux Leakage (MFL) measurements. The MLF technique is probably the most common one, The inspection tool is typically integrated with a carrier that is called a "PIG". PIG is an abbreviation for Pipeline Internal Gauging, an expression derived from prior technology. The PIG with the inspection tool is inserted in the gas flow and will follow the gas flow from the launcher to the receiver end or "PIG-trap".

A magnetic flux leakage inspection tool is built around a set of "brushes" that form a rigid metal construction for being in mechanical contact with the pipe wall. A strong magnetic field is applied to these brushes, each brush pair forming a north and a south pole. In between these poles, a sensor is arranged, capable of measuring the magnetic field. Corrosion or metal loss will change the density and distribution of the magnetic field resulting in a change of the signal from the sensors. The measured signal is either preprocessed before storage or stored directly on a storage medium.

Typical disadvantages with MFL tools are remanent magnetisation and velocity limitations due to induced currents in the pipe wall reducing the magnetisation level.

Ultra sound tools often require a coupling fluid for coupling the signal transducers with the inner side of the pipe wall. When the fluid in a gas pipeline consists mainly of gas, the acoustic coupling with the wall may be rather low due to the low density of the gas.

SUMMARY OF THE INVENTION

The invention is an optical inspection apparatus for internal surveying of a pipeline for transporting fluid. The apparatus comprises an energy supply unit, light source means adapted to form one or more fan shaped beams of light illuminating a line of an interior surface part of said pipeline and optical receiving means positioned outside a plane formed by said fan shaped beams and arranged to have in its field of view the line formed on the internal wall of the pipeline by said fan shaped beam. Optical receiving means generate a plurality of two-dimensional indexed images. Each of said images comprises intensity data for a predetermined number of pixels in each of a predetermined number of lines of said image. A data processing unit includes an image analyzer module with a surface depth profile analyzer module. The depth profile analyzer module is adapted to extract a depth profile of said surface from said recorded images by analysing maxima along the above mentioned lines for obtaining curves representing the lines by positions p(x) of said maxima for each image whereby the positions p(x) of said maxima in the image represents a surface profile. The curves/surface profiles are stored in storage means.

DETAILED DESCRIPTION OF THE EMBODIMENTS OF THE INVENTION

Figure 1:
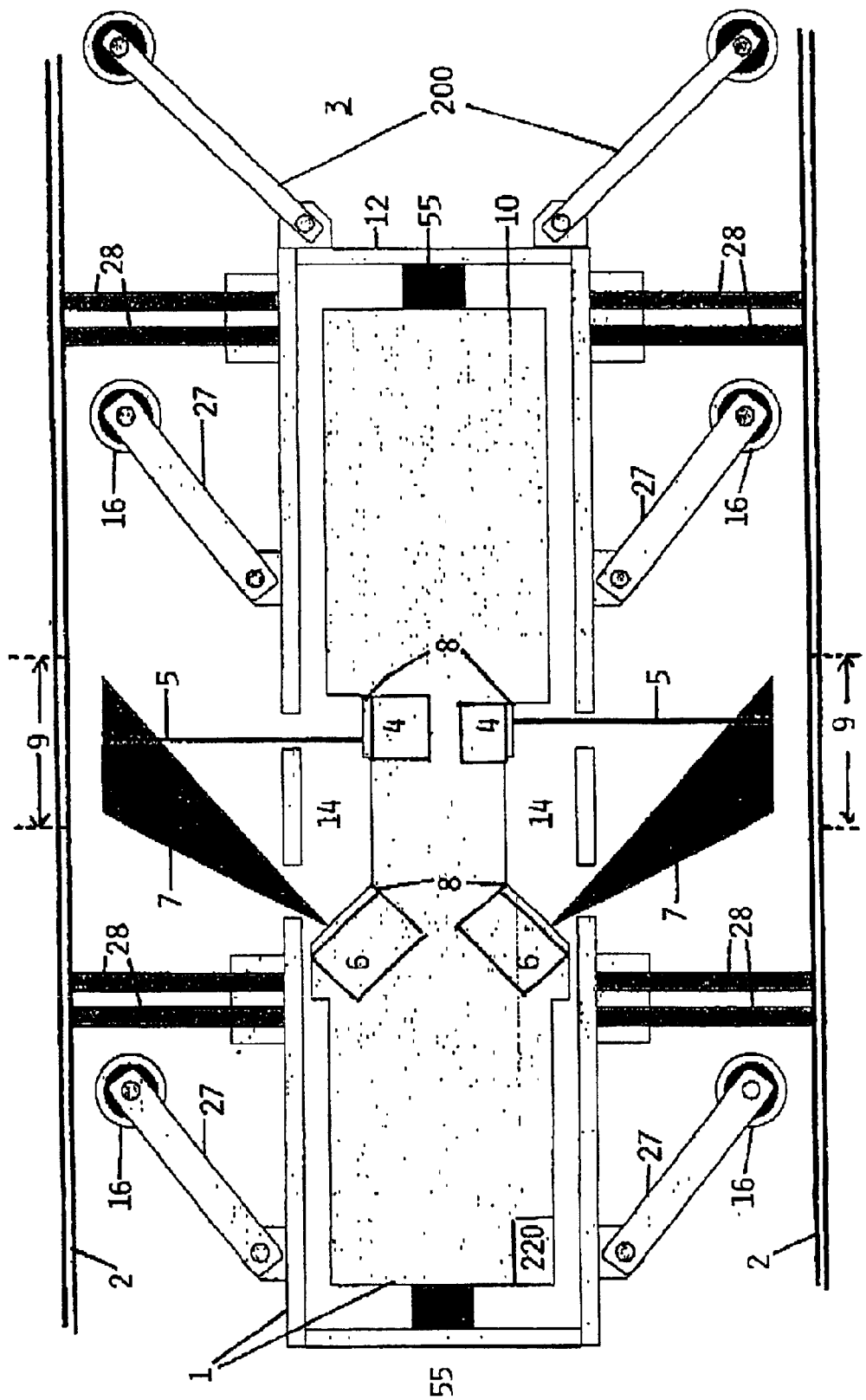
FIG. 1 is a simplified illustration of an optical inspection device according to the invention arranged as a pipeline pig, showing the light illumination by the light source and the field of view of the camera.

FIG. 1 illustrates a typical general sketch of the entire inspection device 1, in the form of a typical Pipeline Inspection Gauge or PIG. Inside the pressure resistant housing 10 of the PIG there are arranged optical components, such as an optical source 4 for generating a beam of light 5, an optical recording unit 6, for example a camera 6 for recording images $20_k$.

The inspection device 1 comprises an outer protective housing or carrier 12. On the outer housing there are arranged wheels 16 attached to the carrier 12 via a spring mechanism 17 or the like to ensure that the wheels 16 are in contact with the pipe 2. Although the spring mechanism 17 can be released such that the wheels 16 are not in contact with the pipe 2 wall as indicated in FIG. 1, during most typical inspection operations the wheels 16 will be in contact with the pipe 2. The carrier also typically has flexible sealing disks 28, typically shaped as an annulus around the carrier and attached to the carrier 12 in order to provide a mechanism whereby the inspection device 1 is driven forward through the pipe 2 when a pressure differential is set up between the front and back of the inspection device. The flexible disks will in most practical situations be more or less bent or deformed and not flat disks as indicated in FIG. 1. In the outer protective carrier 12 there are arranged cut-outs 14 providing openings for fan shaped beams of light 5 and the fields of view 7 of the cameras Inside the outer protective housing or carrier 12 there is arranged a pressure resistant housing 10 which accommodates all active optical components, such as the light source 4 and the camera 6, and all the associated electronics modules for recording, processing and storage of the images 20 recorded by the camera and electric power supply units. Typically, the pressure resistant housing 10 is provided with windows 8 made of sapphire or other strong, transparent material associated with and preferably in front of the camera 6 and light source 4. The cut-outs 14 could be provided with additional optically transparent windows, but these are not indicated in FIG. 1.

Alternatively, the outer protective housing 12 or carrier and the inner pressure resistant housing 10 may be integrated into a single mechanical structure. This will reduce the total volume required by the inspection device 1. This will be beneficial for implementations for use in lower diameter pipes 2.

The inner pressure resistant housing 10 is mounted in the carrier 12 using shock and vibration damping mounts 55. The mounts 55 can be optimized by choice of size, form and material in order to reduce the typical durations, amplitudes as well as mechanical resonance frequencies resulting from the mechanical forces and impulses transferred from the carrier 12 onto the inner protective housing 10 containing all the active optical and electronic parts. The optimization of the mounts 55 could also take into consideration the variation of sensitivity of the inspection tool to the frequency or pulse lengths of the mechanical disturbances. FIG. 1 illustrates two damping mounts 55, one at the each end of the inspection device, however will easily be realized that a larger number of damping mounts may easily well be arranged in the volume between the inner housing 10 and the outer housing 12 in order to optimize the mechanical damping function.

The beam of light 5 generated inside the housing is directed through a first transparent window 8 and onto the inside of a part 9 of a pipe or pipeline 2 for the transport of fluids 3. Seals for the optical windows 8 must be able to withstand the chemical compounds present in the fluid atmosphere 3 that the inspection device 1 will be immersed into (viton in hydro carbons). The camera 6 inside the inspection device 1 has a field of view 7 including part 9 of the internal wall of the pipe or pipeline 2, either through the said first optical window 8 or through a second optical window 8.

Figure 9:
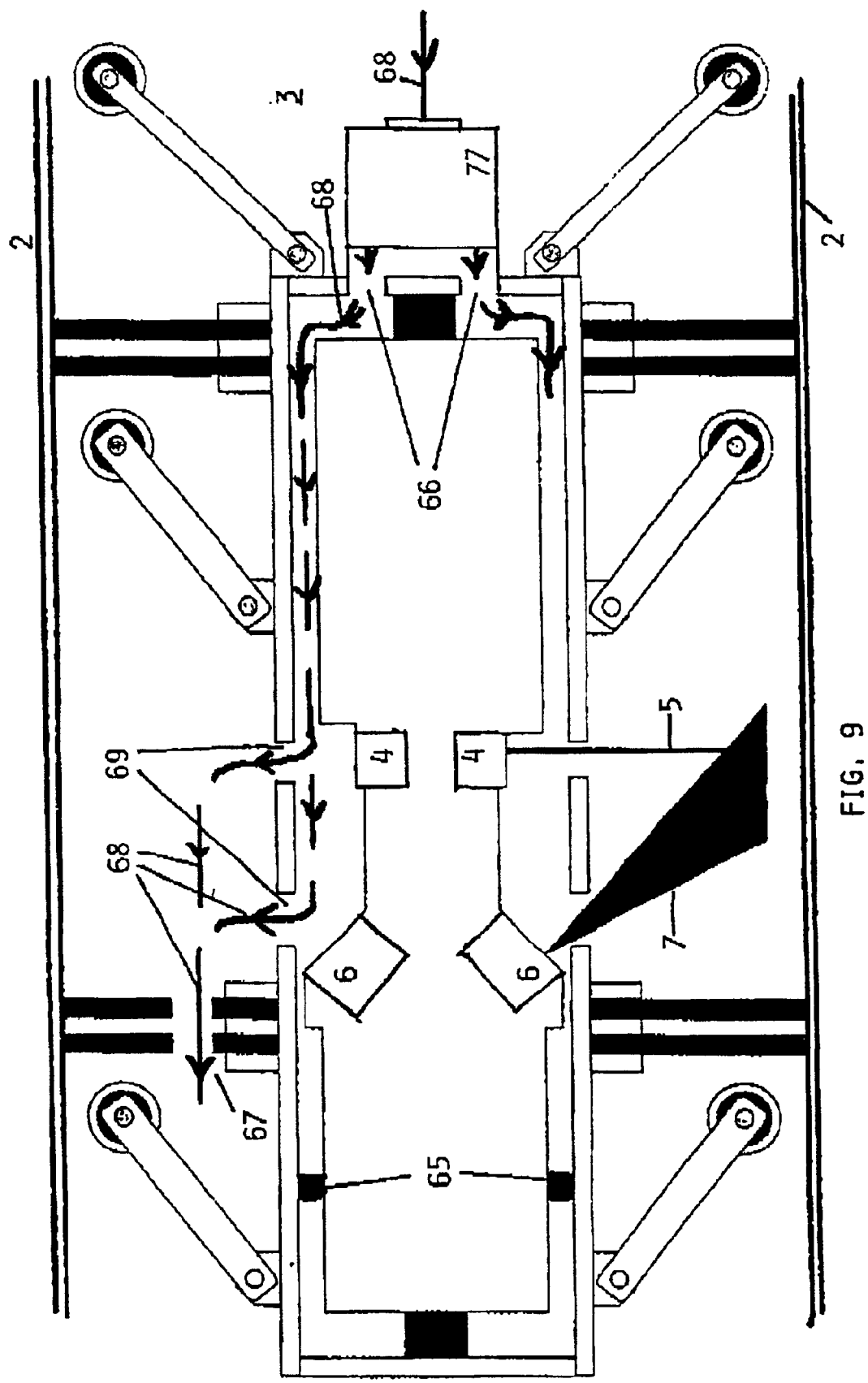
FIG. 9 illustrates a purge flow arrangement for keeping the optical windows of the optical inspection device clean.

Keeping the optical windows 8 relatively clean is essential on an optical system. The differential pressure across the inspection pig is pushing the pig forward. As illustrated in FIG. 9 The differential pressure across the pig can also be utilized to generate a purge flow 68 through the pig via the bypass holes 66,67 thus avoiding that debris settle on the optical windows 8. The bypass purge flow 68 is arranged so that the flow will exit through the cut outs 14 for the lasers and cameras thus pushing debris away from windows 8. The bypass purge flow may contain sticky (non-dry) debris. This could cause deposits on the windows. To avoid debris in the bypass flow from settling on the windows 8, an optional filter unit 77 can be inserted in the path of the bypass flow in order to stop particles or debris.

The invention is an In-Line Inspection device ("Inspection Unit" or "Inspection Tool") for internal inspection of pipelines, typically natural gas pipelines 2, based on optical imaging and profiling technology. Due to the requirements of continuous inspection of long pipelines, cables and umbilical systems may have limited applicability and inadequate for transferring inspection data as well as providing electrical power to the inspection unit. The inspection unit 1 according to the invention is a self contained autonomous unit with its own power source 18,80 as well as sufficiently large storage media 160 for the inspection data. These restraints imply that energy efficiency and image compression are vital aspects for a working system.

Figure 2:
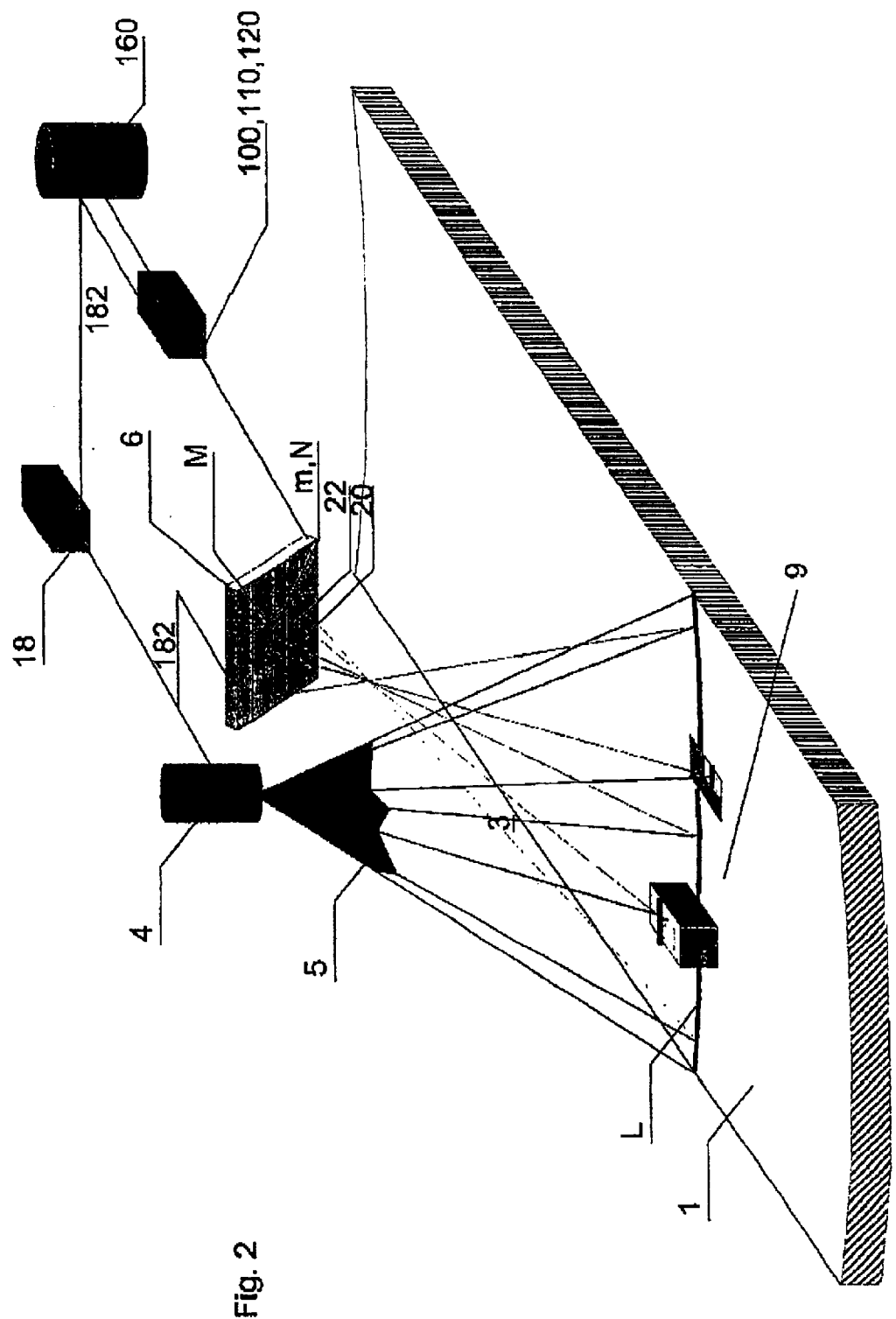
FIG. 2 is a more detailed illustration of the illumination and observation geometry, with a light source generating a fan-shaped beam of light towards the inside of a pipeline, and a camera arranged some distance away from the plane of the fan-shaped beam of beam of light generated by the light source.

FIG. 2 is a more detailed illustration of the basic elements of the invention, which is an optical inspection apparatus 1 for internal surveying of a pipeline 2 for transporting fluid 3. The apparatus 1 comprises the following features: an energy supply unit 18,80 for all components of the pig requiring energy, in this case electric energy. The apparatus has a light source 4 for emitting light. An optical source 4 should be chosen which emits light at optical frequencies in a frequency range where the fluid 3 has at least some transparency, and preferably in a range of high transparency. The light source 4 is adapted to form one or more fan shaped beams of light 5, for illuminating a line profile L of an interior surface part 9 of the pipeline 2. A fan shaped beam may be obtained for example by placing a cylindrically shaped lens in front of the optical source. Other optical components for shaping or forming the light from the optical source 4 into a substantially fan shaped beam could also be used. The interior surface part 9 of the pipeline typically includes surface anomalies or irregularities 17. The inspection device 1 is provided with a camera 6 or other optical receiving means 6 positioned outside the plane formed by the fan shaped beams 5 for receiving the part of the emitted light which is reflected from the inner surface 9 of the pipeline wall 9. The light source means (4) and the optical receiving means (6) are arranged to have their optical axes at an angle of between 0 and 90 degrees, preferably between 30 and 60 degrees with respect to each other.

The surface anomalies or irregularities 17 disrupt an otherwise circular form of the line profile L. The optical receiving means typically consists of a number of smaller sensor elements, each sensor element producing an output signal corresponding to the intensity of light impinging on the sensor element. The output signals are converted into digital signals suitable for processing in the digital signal processing unit 100.

The camera 6 forms consecutive two-dimensional indexed images $20_k$. The index k represents a running image number. Each said image 20 comprises luminosity data for a predetermined number of pixels in each of a predetermined number j of lines M of said image. The camera 6 could be a so-called 3D camera or range camera 6. The light source 4 and the camera 6 are both powered by the energy supply 18 via an electrical connection 182. The energy supply 18 also supplies power to storage means 160 adapted to receive and store digital data from a data processing unit 100. The data processing unit 100 receives image information from the camera 6, either in analogue or digital form. FIG. 2 illustrates the generation of an image $20_k$ at the camera 6. A rectangular section $22_n$ of this image $20_k$ contains an image line N of the laser line L. The dotted line M across the image $20_k$ crosses the image line N at a position, the position varying in dependence on the presence of surface anomalies or irregularities 17 in the pipe section 9.

Figure 3A:
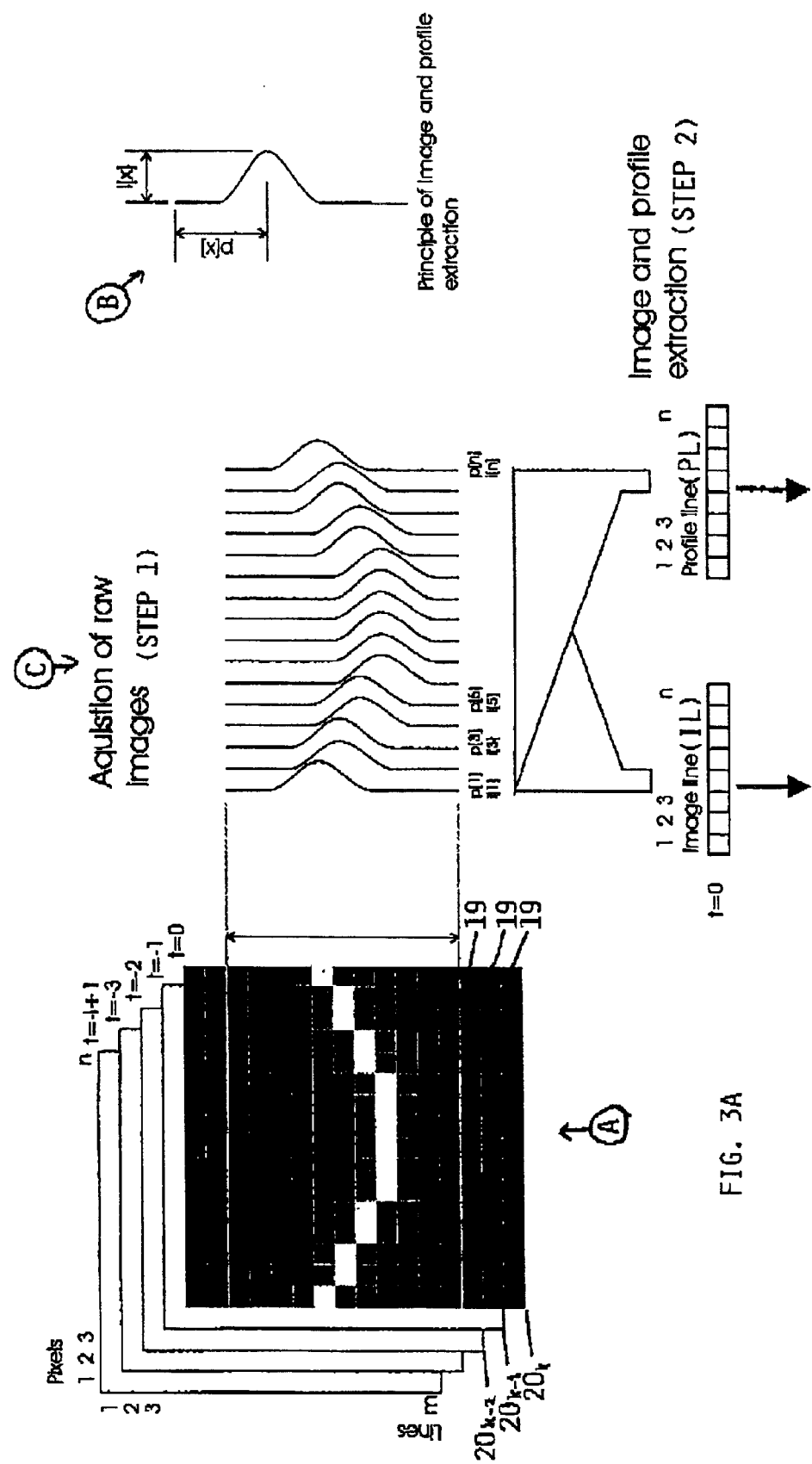
FIG. 3A illustrates the first main steps in the processing of sensor images, from acquisition to image and profile extraction.
Figure 3B:
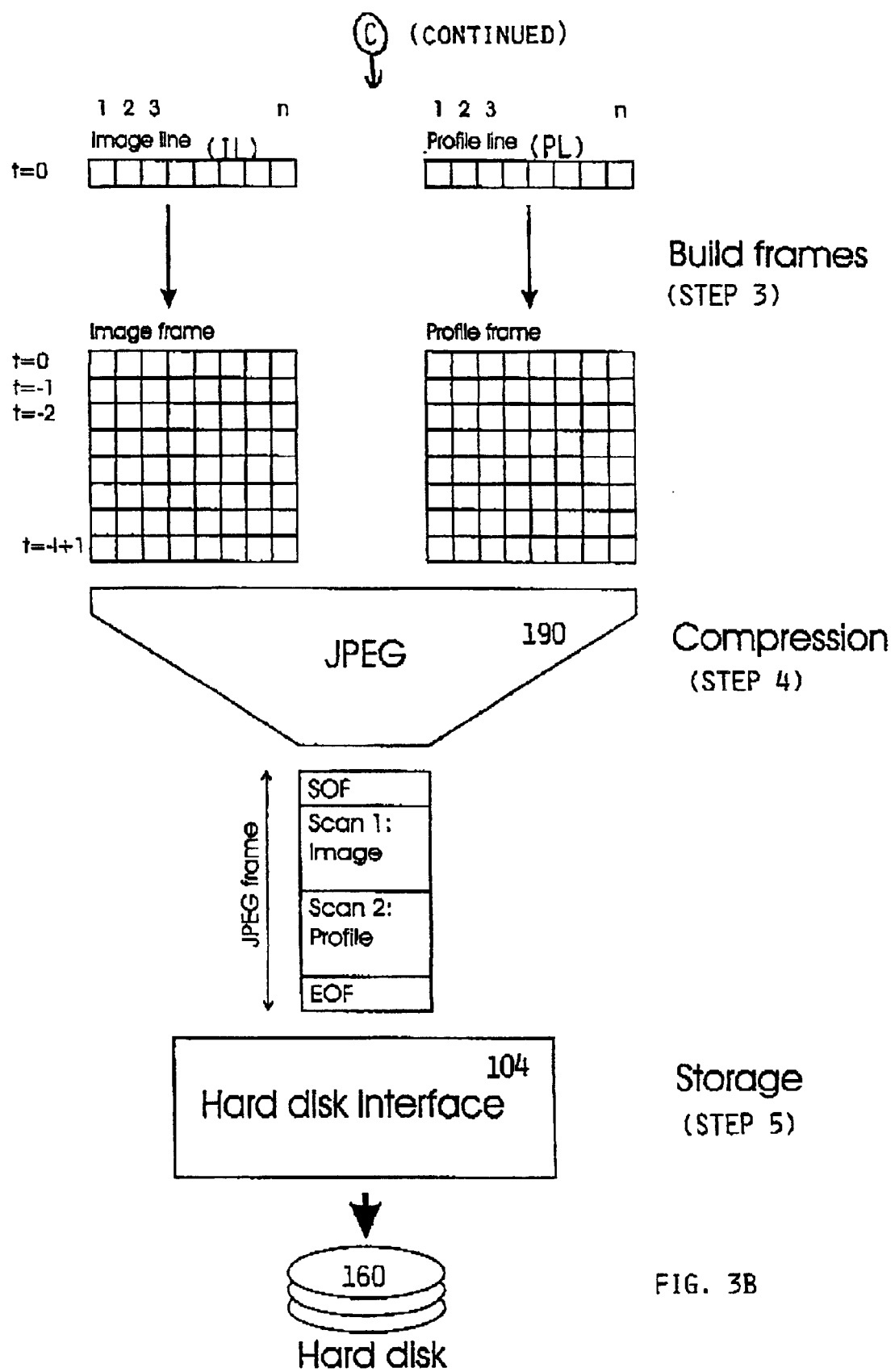
FIG. 3B illustrates the rest of the steps in the processing of sensor images, from image and profile extraction to storage of data.
Figure 4:
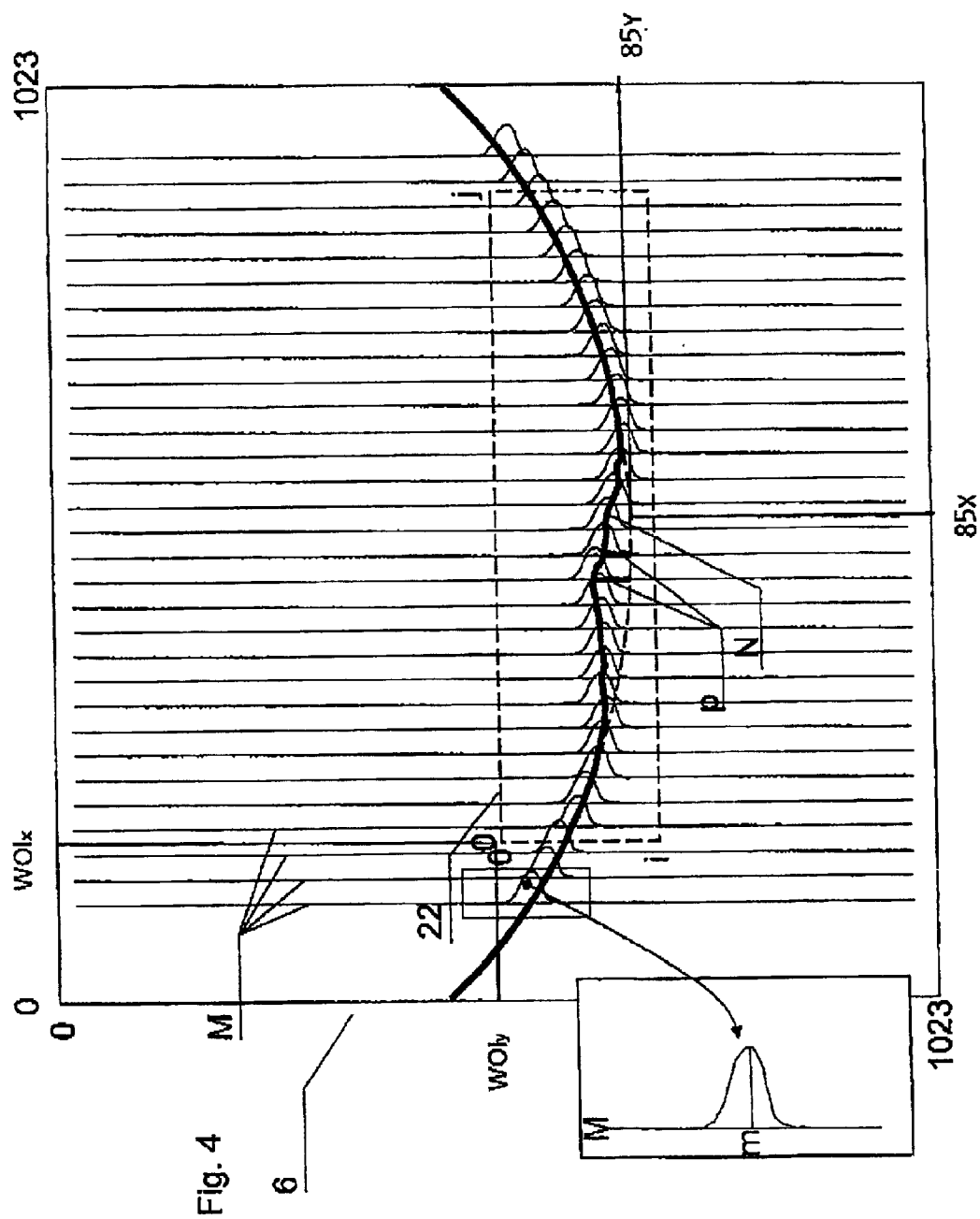
FIG. 4 illustrates a typical image of a line as registered by the camera sensor resulting from the projection a fan shaped beam of light onto the having the pipe wall. The position of the peaks in intensity along each vertical line corresponds to the height of the pipeline wall at that position.

FIGS. 3A and 3B illustrates schematically the main steps in the processing of the images $20_k$ obtained with the optical receiving means or camera 6. At part A are shown in full the last obtained image $20_k$, while previously obtained images $20_{k-1}$, $20_{k-2}$, etc. are indicated behind the image $20_k$. At the top of part C it is indicated how a first step (Step 1) in the acquisition of each image $20_k$ consist of how the image $20_k$, for example 1024×1024 pixel (19) image $20_k$, is reduced to 1024 lines M. FIG. 4 illustrates in more detail how the collection of lines M may look if the image $20_k$ has registered an irregularity or anomaly 17 of the internal pipe surface. As shown in part B of FIG. 3A an image and profile extraction is performed by analysing the peak of each line M in order to identify the position p(x) of the peak and the intensity i(x) of the peak. In the processing diagram of FIG. 3A the image and profile extraction is performed in a second step (Step 2). Performing the image and profile extraction 110,120 on all lines M results in a single line of image data i(x) and profile data p(x) for each image 20, where x is a running index unique to each M line. In a third step (Step 3) illustrated in FIG. 3B a number of image lines i(x) are stacked to obtain a frame of image data. Similarly a number of profile lines p(x) are stacked to obtain a profile frame. The thus obtained image and profile frames are in a fourth step (Step 4) compressed 190 using a JPEG algorithm to obtain a compressed image. In a fifth step (Step 5) the compressed images are received by a interface device 104 which organizes the storage of all compressed images onto a storage unit 160. The interface device 104 is preferably a disk controller 104 and the storage unit 160 is preferably a hard disk 160 or solid state disk 160.

Explained in more detail, a data processing unit 100 receiving the images $20_k$ from the camera 6 has an image analyzer module 110 and a depth profile analyzer module 120. The depth profile analyzer module 120 is arranged for extracting a depth profile of the surface 9 from the recorded images 20 by searching for intensity maxima along each selected line M for determining a curve N representing the laser line L through the identified maxima m. For each image 20 the depth profile analyzer module 120 calculates the depth profile elevations h along N. In this way a large number of selected lines M are reduced to one line of up to 1024 or less depth profile elevations h and luminosity maxima m. The extrapolated curves N, depth profile elevation data with said elevations h and luminosity of said maxima m are sent to a first storage module 160 for storage, and for retrieval at later stages.

The invention uses energy efficient light sources 4, preferably lasers 24. The fan shaped light beams 5 could for example be generated by one or more cylinder lenses arranged in front of the lasers 24 in order to refract the beams of light from the lasers. Each laser beam thus generates a fan shaped beam of light 5 which results in one or more thin lines L on the object to inspect, i.e. the pipe wall 9. The solid state diode lasers 24 are preferably arranged in an array arrangement 25. The light emitting area of the array 25 has a rectangular shape with height-width ratio of about 1:200 in a preferred embodiment. A lens system is placed in front of the laser 24,25 to enlarge the image of the laser array 25 and project this enlarged image onto the pipe wall 9. The projection on the pipe wall 9 in this case will also be a thin illuminated line L with the same height-width ratios as the light emitting areas of the lasers 25. Even though lasers 24 are the preferred light sources from the point of view of providing a thin beam of light 5 of high intensity, even a LED (Light Emitting Diode) or LED array with beam forming optics could suffice in some applications. By placing the cameras 6 outside of the plane formed by the fan shaped laser beams 5, in this embodiment behind the laser plane when looking forward, see FIG. 2, positions with different height on the pipe wall 9 will appear at different positions with different vertical position (or height) on the image sensor 11. The image N of the laser line L on the image detector can be found by detecting the position of that particular pixel (19) in each column which has the highest light intensity. Having identified this pixel (19) with the highest intensity and using knowledge about the geometry of the set-up as well as the pixel (19) size, the real positions of the intersection line between the laser plane 5 and the pipe wall 9 can be calculated. In a flawless pipe these positions lie closely along a circumferential section of a circle. In a pipe having flaws, these positions will depending on the sizes and shapes of the anomalies or irregularities 17 of the pipe wall 9, thus deviating from the case of the flawless pipe.

Figure 10:
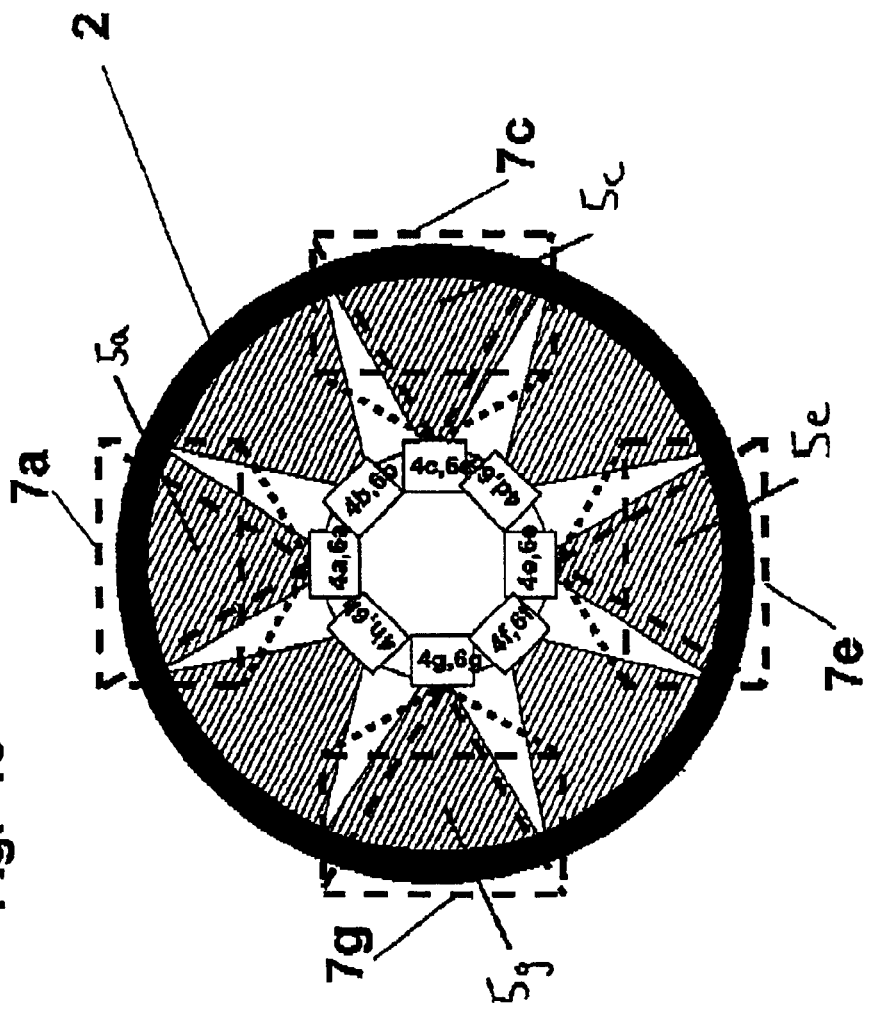
FIG. 10 illustrates a cross-section of an optical inspection device according to the invention inside a pipe showing the several light sources and cameras.
Figure 11:
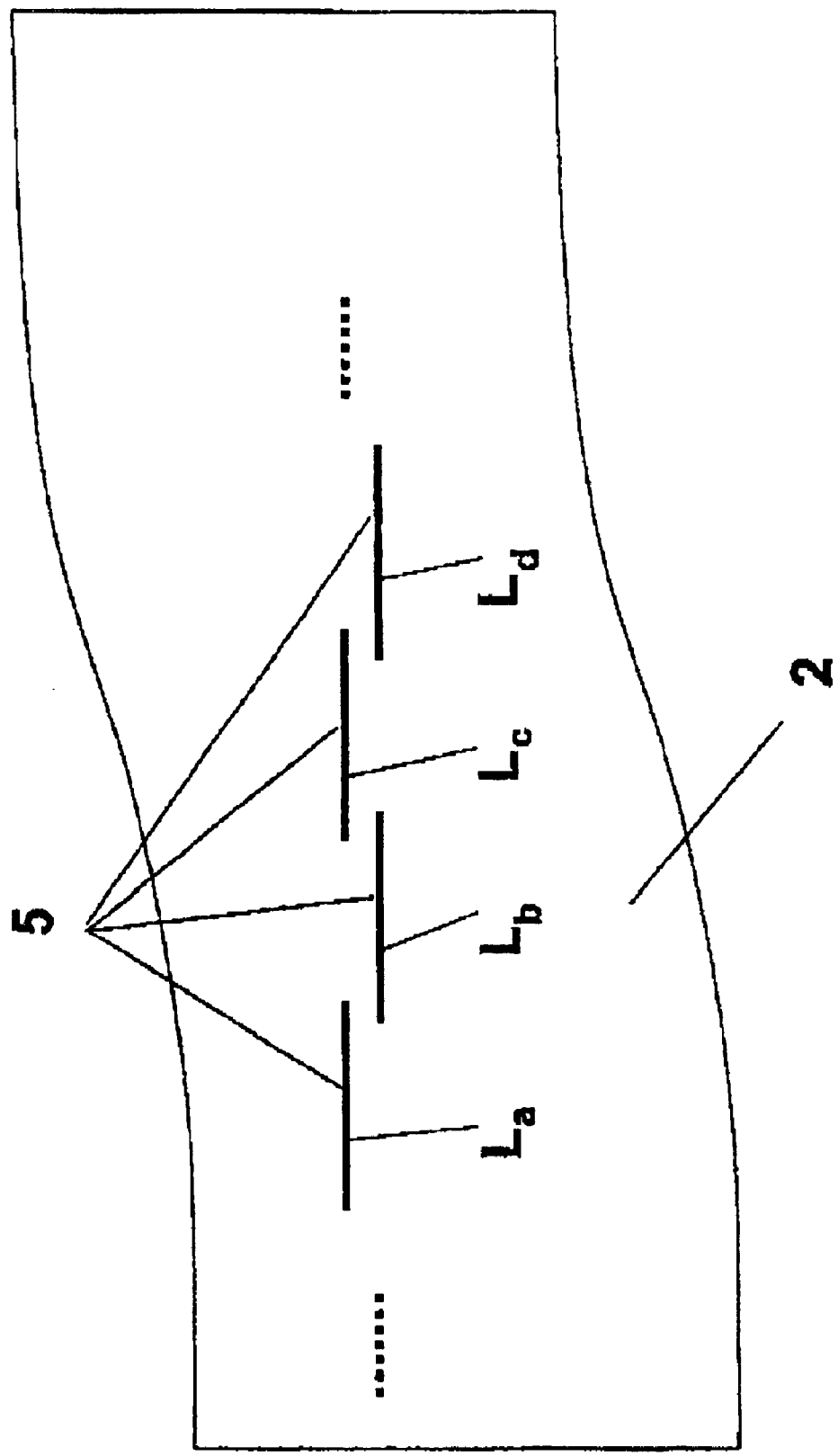
FIG. 11 illustrates schematically the resulting laser lines from the arrangement in FIG. 10 in a folded out section of the pipe 2.
Figure 12:
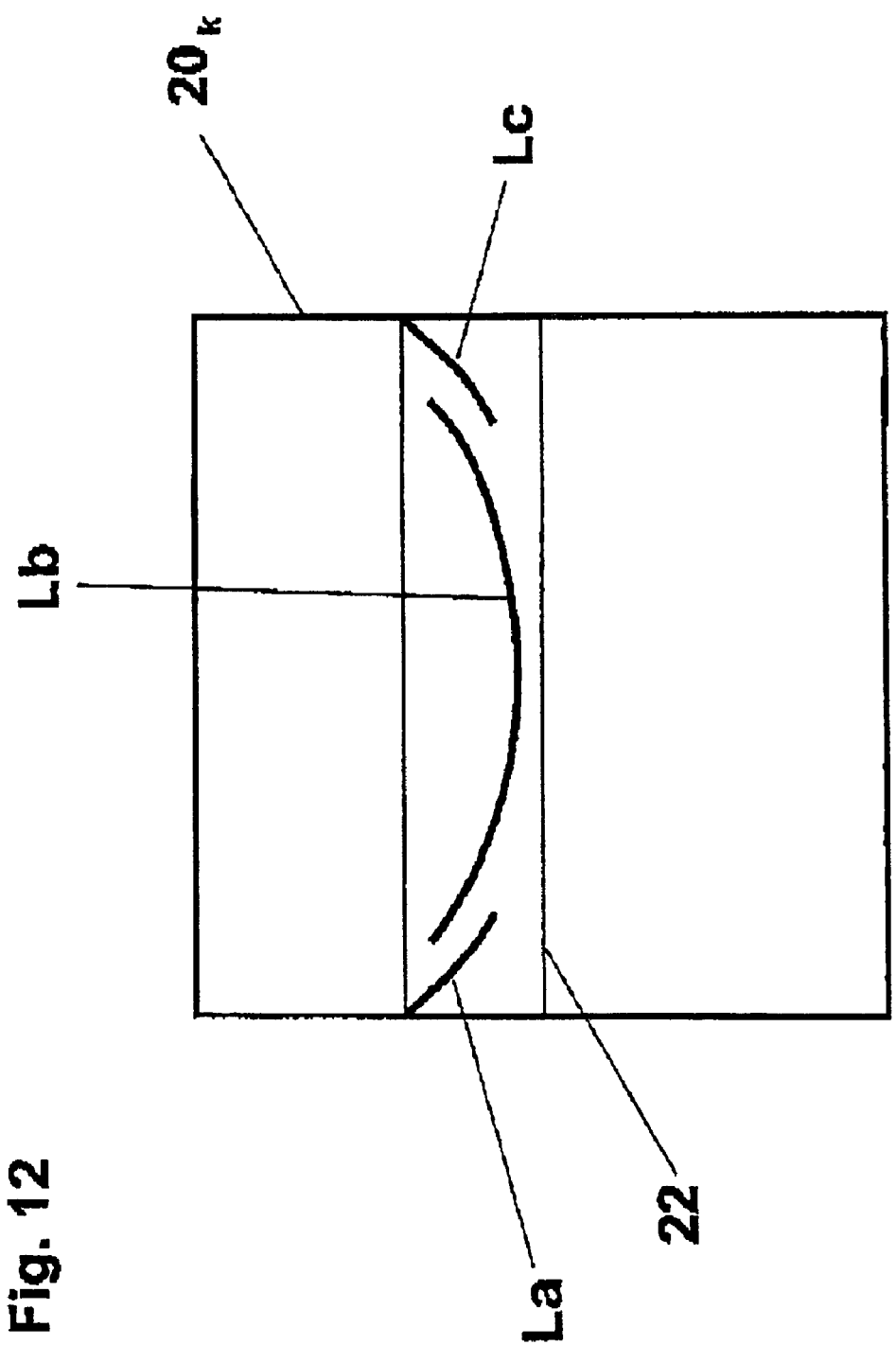
FIG. 12. illustrates a typical image obtained with the camera using an arrangement according to FIG. 10.

Several light sources 4a,4b,4c,4d, . . . and corresponding cameras 6a,6b,6c,6d, . . . may be arranged to illuminate and image around the inner periphery of the pipeline 2 as illustrated in FIG. 10, in which each pair of light source and camera 4a–6a, 4b–6b, . . . are associated with corresponding fan shaped beams of light 5a,5b, . . . and corresponding fields of view 7a,7b,7c, and 7d of the cameras 6a,6b,6c and 6d, respectively. The illuminated lines L generated by the fan shaped beams 5 from laser sources 24,25 are in this context referred to as laser lines. The fan shaped beams of light 5a, 5b, will typically be displaced longitudinally with respect to each other in the pipeline 2 in order to avoid overlapping of the laser lines L. This is illustrated schematically in FIG. 11 illustrating schematically a fold-out of the section 9 of the pipe 2 and the laser lines $L_a$, $L_b$, $L_c$ and $L_d$ corresponding to the light beam 5a, 5b, 5c and 5d respectively, and corresponding to light source and camera pairs 4a,6a, 4b,6b, 4c,6c and 4d,6d respectively. FIG. 12 illustrates schematically a typical image obtained by the camera in the case that several light sources and cameras are used. In the centre of the image is the laser line 5b. At the edges of the images parts of neighbouring laser lines 5a and 5c overlap slightly. Using such an arrangement of a plurality of light sources and cameras the entire periphery can be scanned in one run by the inspection device 1.

Once the intensity profile across the thin laser line generated by the illumination of the laser 24 is known, i.e. registered and stored, a several techniques can be utilised to improve the precision of the position of the maximum to sub pixel resolution. This requires that the image of the laser line L must be somewhat thicker than the equivalent of one pixel width on the camera sensor 6.

In the simplest embodiment the position of the maximum of along each line M is obtained by simply finding the maximum value.

In a further embodiment the position of the maximum along each line M can be improved by convolution of each line M with a reference light distribution. The position where such a convolution gives a maximum value is taken to be the improved position of the maximum.

Figure 5:
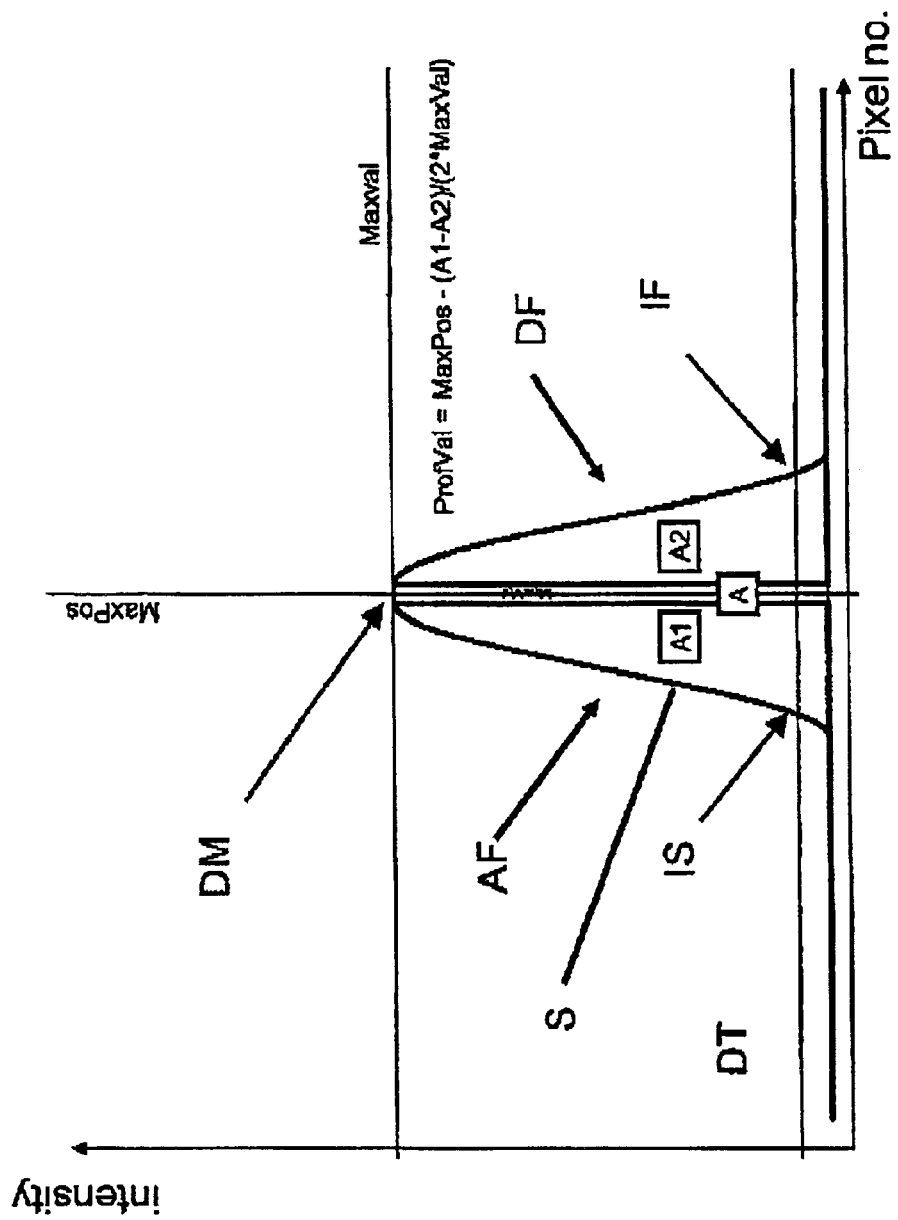
FIG. 5 illustrates schematically a signal processing scheme to improve the determination of the position of the maximum point in each camera line.

Yet another embodiment for determining the position of the maximum along each line M is illustrated in FIG. 5. The technique is based on integration of the area formed by the ascending and descending flanks A1,A2 of the image line S of the laser line L. A detection threshold DT is set. When the signal crosses the detection threshold DT at IS an algorithm starts integrating the area A1 below the ascending flank AF of the signal line S. The integration stops when having detected a maximum intensity (MaxVal) at DM with its corresponding position (MaxPos), and the integrated area is called a first ascending flank area A1. The area after passing the maximum intensity DM along the descending flank DF is called the descending flank area A2. The integration of A2 finishes when the signal passes below the detection threshold DT at IF. Now an improved position of the maximum, or profile value (ProfVal) can be calculated using the equation $$ProfVal = MaxPos - (A1 - A2)/(2*MaxVal)$$

The collection of all the profile values obtained for the corresponding collection of lines M, is gathered in a profile line p(x) as indicated in FIG. 3, where x is a running index of the lines M in each image $20_k$.

In addition to the profile information the cameras 6 additionally find and store the grey levels at the height positions corresponding to the found laser line L. The integrated areas A1 and A2 as obtained with the technique described above can be scaled to represent the maximum m along one line M in the camera.

The collection of all the maxima m for the corresponding collection of lines M results in an image line i(x) as illustrated in FIG. 3. The values of i(x) correspond to the grey levels of the image line along the laser line L on the pipe wall.

By moving the camera and laser system a small distance and then making a new exposure a new profile and a new grey level image line is obtained. By placing these and consecutive image lines next to each other we can form a continuous still image of the pipe wall as well as continuous 3d dimension maps from the profile data. Placing lines next to each other is illustrated in FIG. 3 by the "Build Frames" step 3 in FIG. 3.

Due to power considerations regarding the laser sources 4 and the distribution of the light around the internal circumference of the pipe 2 there is a requirement for using several lasers 4,24. In order to avoid time consuming and elaborate alignment of the laser lines the fan shaped beams 5 are arranged in different planes. To accommodate pipes 2 of various diameters with the same unit each laser beam 5 will overlap into neighbouring cameras 6. This means that each camera 6 not only sees the laser line L of its associated laser 4, but that it also sees the laser lines L of the two lasers 4 associated with the neighbouring cameras 4. Detecting a laser line $L_b$ with one camera 6b and the associated light source 4b and laser lines $L_a$ and $L_c$ from the neighbouring light sources may lead to problems determining which laser line to select. One method of avoiding this problem would be to chose the scanning direction such that the line from the laser associated with the camera in question is detected before the lines from the neighbouring lasers are detected. The first valid profile value found, will be from the laser line that corresponds to the camera.

The camera 6 and its electronics find the profile p(x) and image data i(x) from a larger two-dimensional image $20_k$ and then these two data streams are processed separately. Prior to storage the profile data p(x) and image data i(x) are compressed. The profile data and image data may be combined in compression process. The compression process may be a lossy or a lossless process. If a lossy process is found to give adequate representation of the pipe surfaces such a process will normally require a lower memory capacity. However, if it required that no information is lost in the compression process a lossless compression technique has to be chosen. The preferred embodiment for this invention uses JPEG compression for both image and profile data.

As the camera sensor 6 is a two-dimensional sensor, in the preferred embodiment 1024×1024 sensor elements arranged in a two-dimensional matrix form, only one profile line p(x) with position information and one image line i(x) with grey level data are being stored from each exposure. Assuming a resolution of 1 mm is required along the pipeline 2, one exposure per mm pipeline will be needed. Comparing the size of the original image $20_k$ from the sensor 11 with the size of the image and profile lines, i(x) and p(x) respectively, it is easily understood that the amount of data has been reduced by orders of magnitude. This is achieved while maintaining significant information. However all data from the sensor 11 normally should be read out and undergo signal processing. This takes processing time and for most sensors 11 the number of pixels that has to be read out limits the frame rate, i.e. the number of exposures per second. In most cases the range of pipe diameters in one inspection run is limited as well as the expected size of anomalies.

Using an image sensor 11 with a programmable window of interest (WOI) 22, only the pixels in the WOI 22, as illustrated in FIG. 4, will be read out thus increasing the attainable frame rate. The position of the window of interest (WOI) is defined by an x-coordinate $WOI_x$ and a y-coordinate $WOI_y$. $WOI_x$ and $WOI_y$ are typically pixel column and row numbers of the image 20. The window of interest (WOI) in FIG. 4 has size j×i, i.e. it is j pixels wide and i pixels high.

Figure 6:
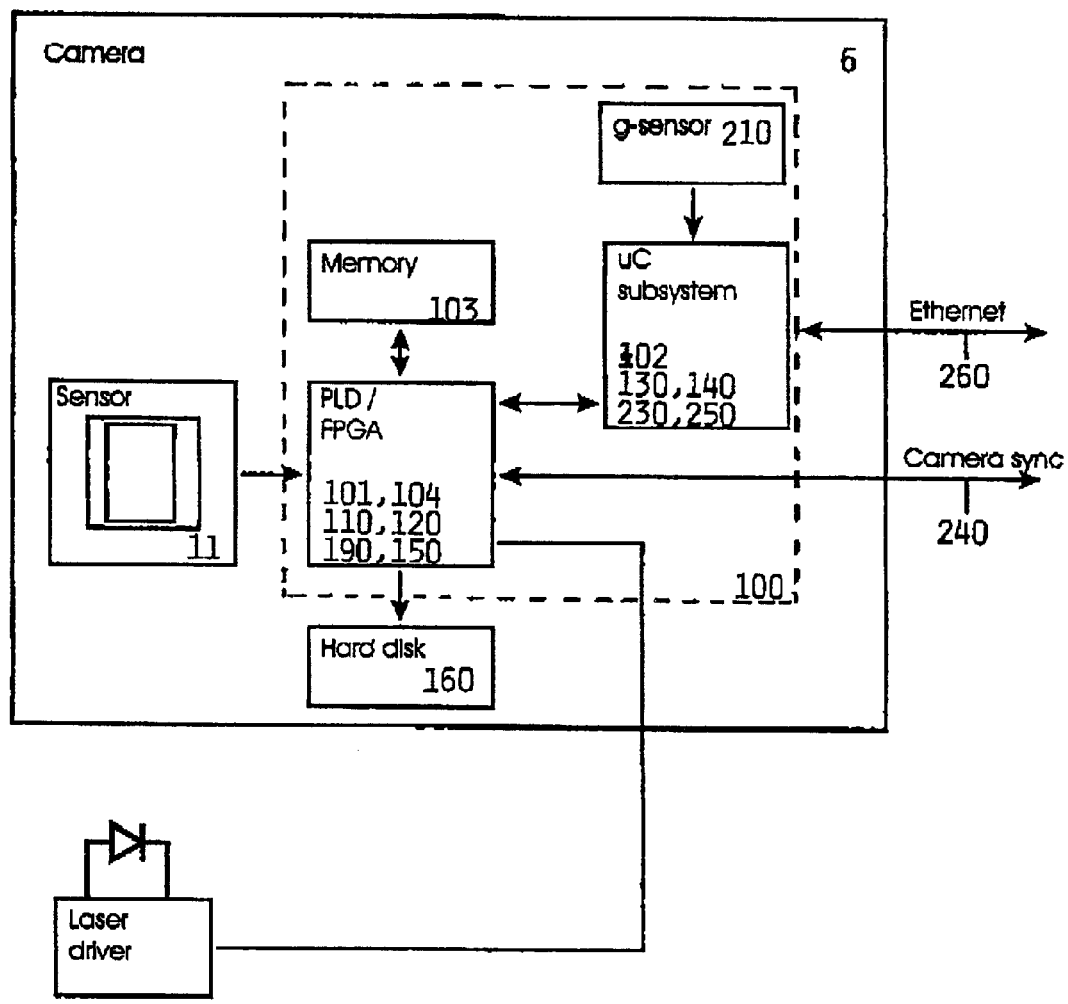
FIG. 6 is a block diagram of camera and laser driver modules of the invention.
Figure 7:
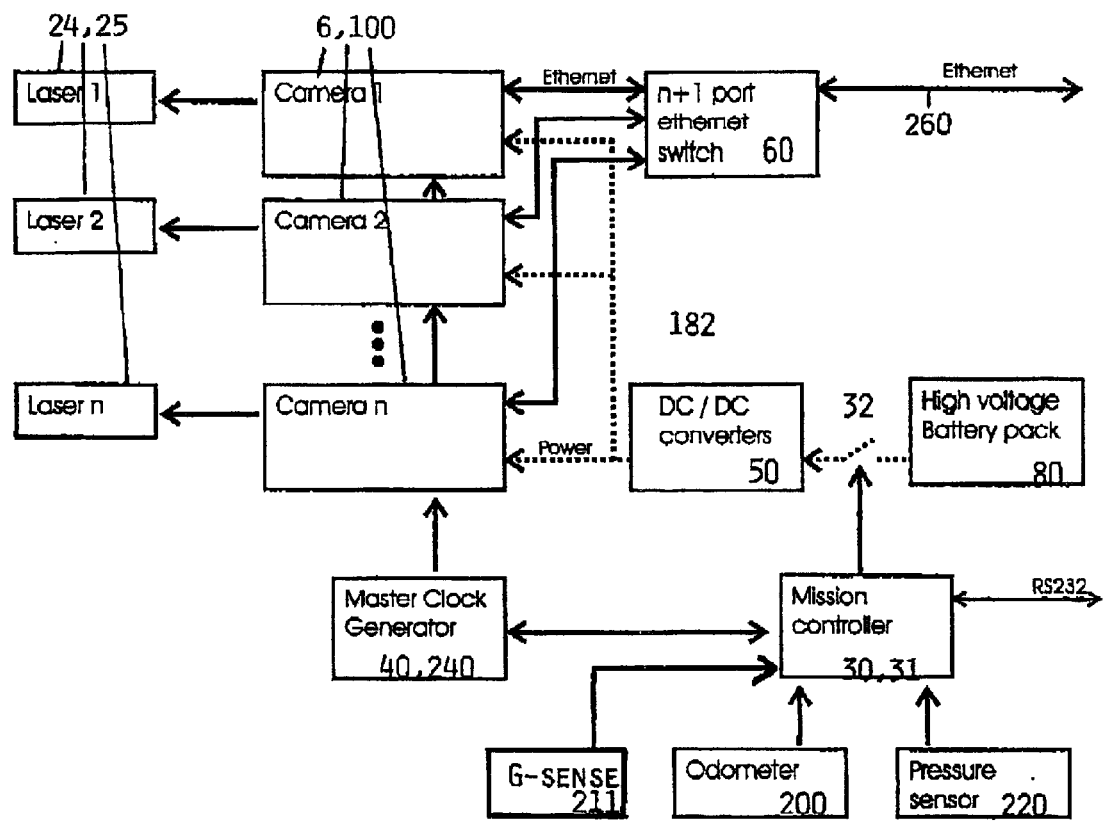
FIG. 7 is a block diagram of a complete inspections system.

The data processing unit 100 of FIG. 6 and FIG. 7 thus includes image pixel intensity evaluation means 130 for identifying bright or high intensity pixels in the full image $20_k$. This could for example be achieved by identifying the pixels having intensities above a chosen threshold value DT.

The processing unit 100 also includes selecting means 140 defining image parts or image segments $22_n$ of each said image $20_k$, in which each image segment $22_n$ comprises at least several bright pixels as identified by the image pixel intensity evaluation means 130. The selecting means 140 for selecting an image segment $22_n$ comprising the whole of or part of said line profile L is closely associated with position determining means 150 for determining a position of the image of the line profile L within an image segment $22_n$ or within the entire captured corresponding image $20_m$ in the camera 6. The selecting means 140 thus is arranged to find rectangular areas or sections 22 in the larger image 20 that will contain a collection of pixels with high intensity. In addition the position determining means 150 can be adapted to determine any change of position 85x,85y of the curve N from one said image $20_m$ to a subsequent image $20_{m+1}$ and to redefine said defined image segment $22_n$ in order that the curve N is maintained within the image segment $22_n$.

In addition to the programmable window of interest (WOI) 22 this invention has also an automatic adjustment of the WOI 22 so that it could be made somewhat smaller and increasing the frame rate even more. Such an automatic adjustment could for example be achieved by tracking any shift in the position of the high intensity pixels within the window of interest (WOI) 22. Once high intensity pixels within the window of interest (WOI) approaches the edges of this defined window 10, the size or position of the window is adjusted correspondingly to ensure that the majority of high intensity pixels lie within a chosen pixel distance from the edges of the window. In a similar manner, the size of the WOI 22 could be reduced if it is found that the WOI 22 contain large areas along its edges having no or very few high intensity pixels.

Utilizing the concept of automatic adjustment of the window of interest (WOI) 22 also makes inspection of multiple dimension pipelines 2 possible. This is referred to as multi dimensional pigging. The algorithm controlling the location of the WOI 22 will make sure that the image of the laser line is contained within the WOI 22.

The invention thus is provided with means for identifying a change of position of the line profile L from one of said images $20_m$ to a subsequent image $20_{m+1}$, and means to move the image segment $22_n$ containing the line profile L in order to follow the change of position of the line profile L.

As described above, the apparatus according to the invention comprises means to reduce the amount of image data analysis by transmitting from said images $20_k$ to said image analyzer module 110 and depth profile analyzer module 120 only the data from said image segment $22_n$.

As illustrated in FIG. 6 the camera 6 includes an image detector 11 which could be of a CMOS type with built in analogue to digital conversion, but it could alternatively be realised as a CCD type detector with separate analogue to digital converters (ADC). The electronics of each camera 6 is built around a field programmable gate array device (FPGA/PLD) 101 and a microprocessor 102. The microprocessor 102 is handling top-level control of the camera 6 like finding the laser line L and then continuously tracking it. The microprocessor 102 is also performing the exposure measurement and control 230 by regulating the output of the lasers 24,25. An exposure control 230 is required to avoid underexposed and overexposed images 20 from the sensor 6. Underexposed images might lead to that the line on the sensor could be so dark that it in full or partially will not be detected thus resulting in malfunction of the device. Overexposed images will lead to that the line on the sensor 6 will saturate and possibly be wider resulting in lower accuracy of the profiling procedure. Extreme overexposure might result in severe stray light and/or ghost images capable of disturbing the profiling procedure.

The exposure control means 230 will in the basic implementation regulate the exposure so that the average grey level is 50% of maximum intensity of a pixel. A more advanced implementation might consider statistical information like pixel value (histogram) distribution and optimize for the lowest number of underexposed pixels thus avoiding total lack of profiles in underexposed areas.

The real time image processing tasks are being performed in hardware in the FPGA/PLD 101. Tasks performed in the FPGA/PLD 101 are imaging and profiling including improvement of the resolution, sub-sampling. The FPGA/PLD 101 compresses 190 image and profile data using the JPEG algorithm. The FPGA/PLD 101 also contains hard disk controller circuitry 104 that is being used for controlling the hard disk 160 where image data i(x) and profile data p(x) are stored. Associated with the FPGA/PLD is a memory block 103. After the digital circuitry in the FPGA/PLD 101 has completed the calculation of the profile and image lines, the profile and image lines will be buffered in the memory 103 waiting for JPEG compression in the JPEG compression block 190. When the JPEG compression block 190 is ready, the data will be read back from the memory 103 and will be compressed. The output from the JPEG block 190 are JPEG compressed image and profile data and this compressed data will then be buffered (once more) in, the memory 103 waiting to be written to the hard disk 160. When the hard disk controller 104 is ready and enough data has been buffered to fill one hard disk block, one block of data is first read back from the memory 103 and then written to the hard disk 160.

The FPGA/PLD 101 also generates line numbers so that image lines from different cameras 6 can be synchronised. The cameras 6 are divided into two groups, one called master camera, and the rest are considered to be slave cameras. The master camera will transmit line numbers to all the slave cameras. If no line number is received by the slave camera it will generate its own line number.

Several of the processing blocks mentioned, e.g. the image analyzer module 110, the depth profile analyzer module 120 can be realized as software program modules running on a microprocessor. However, these modules will preferably be implemented as hardware, for example in an application specific integrated circuit (ASIC) in order to optimize the speed of these operations while minimizing the power consumption. The compression 190, the image pixel intensity evaluation means 130, the selecting means 140, the position determining means 150 can be realized as software program modules running on a microprocessor or microcontroller, however, these modules can also be wholly or at least partly implemented in hardware.

In the preferred embodiment the master camera is substituted for a central exposure clock and line number generator 40, as illustrated in FIG. 7 in order to synchronise image data from the different cameras 6. This unit can is called the master (exposure) clock generator 40. The master clock generator 40 will send a line number to the cameras 6. When the camera 6 has received the full line number in serial form and verified the checksums it will initiate a new exposure. Each camera 6 will store the line number together with the image data i(x) and profile data p(x).

If a camera 6 detects that the central line number generator 40 does not function, it will generate its own line numbers. It is also possible to configure one of the cameras 6 to function as a "master" camera generating line numbers for the other cameras 6.

Using the master clock generator 40 all the cameras 6 may be operated in synchronism by the transmission of a line synchronization clock signal from the master clock generator 40 to all cameras 6. In addition the master clock generator 40 may transfer an accompanying line number to the cameras 6. Cameras 6 receiving the line numbers may use these numbers as tags associated with each image line i(x) and profile line p(x) such that the image line and profile line are stored in the storage media 160 together with the line number. The line numbers hence may function as tags for being used at later stages in order to align image and profile data from individual cameras 6, and for performing processing on a larger number of lines, for example the correlation of data from different cameras 6 in the case that one camera was out of function for a short period.

The FPGA/PLD circuitry 101 shown in FIG. 6 will also generate statistical image information that is used by the exposure control and the line tracking (WOI selection).

In the preferred embodiment the microprocessor 102 also has a high speed Ethernet connection 260 as illustrated in FIG. 7 which is used for communication between cameras as well as for downloading data from the hard disks 160.

The power supply system 18 is built around high energy density power sources 80 that typically will be Lithium(Li) batteries. Several cells are connected in series to obtain a relatively high voltage that is close to the maximum input voltage the voltage regulators can handle. In the preferred embodiment high efficiency DC—DC converters 50 are placed near the consuming printed circuit boards with the highest possible voltage on the power cables 182 from the batteries 80. Energy loss in the power cables 182 is reduced by having a higher voltage on the longer power distribution wires.

Additional means for turning the system on an oft is also a part of the system. In the preferred embodiment this unit is a mission controller 30 that can start and stop the recording by turning the camera recording on and off, preferably realized as a programmable microprocessor 30. The mission controller 30 can be provided with internal timers 31 set to count down to zero at chosen times. The timers 31 could be pre-programmed prior to launching the inspection device 1 into the pipeline 2 or the timers 31 could be triggered during the inspection by chosen events. Pressure sensors 220 illustrated in FIG. 1 arranged for sensing the pressure around the inspection unit 1 could provide signals to the mission controller 30. An odometer 200 may be included in the inspection device 1 as illustrated in FIG. 1 and arranged to provide the mission controller 30 with information related to the distance travelled or velocity of travel. Depending on the distance travelled or velocity of movement the mission controller 30 can turn the cameras 6 on and/or off. Data from the odometer system can be used for navigation as well as means for adjusting the line frequency according to current tool velocity so that the longitudinal resolution remains constant. If the inspection speed is known to be relatively constant a fixed line frequency can be used.

The inspection device 1 could also be fitted with accelerometers 210 integrated in each camera 6, as illustrated in FIG. 7 for detecting the acceleration or rotation of the inspection device 1. for example caused by the device encountering obstacles inside the pipeline 2, for example objects floating in the fluid 3 inside the pipe 2, large damaged section of the pipe 2 or the like. The readings from the accelerometers 211 could be supplied to the mission controller 30 which in given situations will close down the operation of one or more cameras 6.

Figure 8:
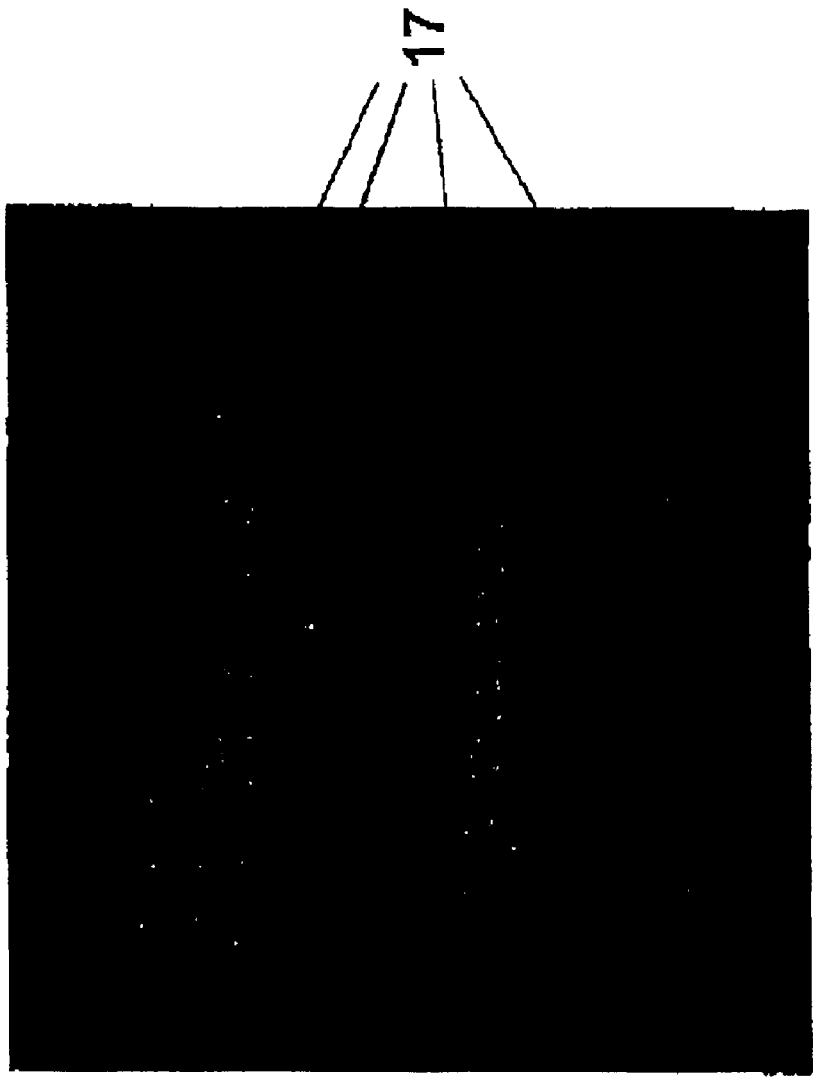
FIG. 8 illustrates a combined image built up from several line images according to the invention, illustrating a cavity and a protrusion on the inwards facing pipeline wall.

Following a pipeline inspection operation using the inspection device 1 according to this invention and when the inspection device 1 is accessible, for example in a pig trap, the data from the storage media 160 of the inspection device 1 can be downloaded via any suitable data communications link, e.g. IEEE 1394, Ethernet or any known combination of hardware and software for data communications. In the present invention a 100 Mbit Ethernet link 260 has been chosen. The data stream from each camera 6 is supplied to the Ethernet using an n+1 port Ethernet switch 60 as illustrated in FIG. 7. A typical resulting image built up from a combination of several line images as described according to the invention, illustrating a cavity and a protrusion on the inwards facing pipeline wall is illustrated in FIG. 8.

In an alternative approach also supported by this invention is to de-mount the storage media 160 from the inspection device 1, i.e. the pig, and connecting the storage media 160 to a separate computer. The computer may then transfer the data on the de-mounted storage media 160 onto a working storage medium on the computer itself, onto backup storage media, e.g. using any data storage facility readily available for use in combination with a computer, possibly a portable computer.

Following the copying of the recorded data from the storage media 160 used during the inspection, the data may undergo further processing. Such further processing could for example be the building of a database suitable for use with display software in order to enable the display of grey level images as well as 3D profiles to an operator.

The further processing could also comprise a comparison of the data with a previously established database of typical results in order to classify the new results according to the types of results obtained. Depending on the possible abnormalities found, these could be classified by an image processing software, for example according to a set of previously determined rules. In particular, this is intended to assist an operator in evaluating the severity of the abnormalities.

The pressure resistant housing of the inspection device 1 should in addition be equipped with an overpressure valve. Such a valve is a personnel safety precautionary arrangement to protect from possible harmful effects of an unintentional internal pressure build-up. An internal pressure build-up may for example be caused by leakages into the pressure housing. Such a pressure could typically happen during the operation inside a pipeline at high operating pressures. Another precautionary safety measure is to provide the housing with purge nipples thereby making it possible to purge the interior of the tool with inert gas. This reduces the risk of mixing air/oxygen inside the housing with potentially explosive gases leaking into the housing from the pipeline.

For higher reliability the system is also equipped with watchdog circuitry that restarts electronic system components that has stopped working properly due to brown out conditions or software bugs.

What is claimed is:

1. An optical inspection apparatus (1) for internal surveying of a pipeline (2) for transporting fluid (3), said apparatus comprising;
an energy supply unit (18);
a light source means (4) adapted to form one or more fan shaped beams of light (5) illuminating a line (L) of an interior surface part (9) of said pipeline (2);
optical receiving means (6) positioned outside a plane formed by said fan shaped beams (5) and arranged to have in its field of view (7) the line (L) formed on the internal wall of the pipeline (2) by said fan shaped beam (5);
said optical receiving means (6) adapted to form a plurality of two-dimensional indexed images ($20_k$), said index k representing a running image number, each of said images (20) comprising intensity data for a predetermined number of pixels in each of a predetermined number of lines (M) of said image (20);
a data processing unit (100) including an image analyzer module (110) with a surface depth profile analyzer module (120), said depth profile analyzer module (120) adapted for extracting a depth profile of said surface (9) from said recorded images (20) by analysing maxima (m) along said lines (M) for obtaining curves (N) representing said line (L) by positions p(x) of said maxima (m) for each image (20) whereby the positions p(x) of said maxima (m) in the image represents a surface profile (N);
a first storage means (160) for storing of said curves/surface profiles (N).

2. Apparatus according to claim 1, comprising data processing means (100) adapted to reduce the amount of image data stored whereby only the data associated with the obtained curves (N) are stored.

3. Apparatus according to claim 1 wherein the light source means (4) and the optical receiving means (6) are arranged to have their optical axes at an angle of between 0 and 90 degrees, preferably between 30 and 60 degrees with respect to each other.

4. Apparatus according to claim 1 wherein the data processing unit (100) comprises;
image pixel intensity evaluation means (130) for identifying pixels (19) of high intensity along each said line (M);
selecting means (140) for defining rectangular sub-images or segments ($22_n$) of each said image (20), where each said image segment ($22_n$) includes a number of said identified pixels (19) of high intensity;
said selecting means is adapted for selecting an image segment ($22_n$) comprising the whole of or part of said curve (N);
position determining means (150) adapted for determining a position (85) of said curve (N) within said image segment ($22_n$) or within said corresponding image (20).

5. Apparatus according to claim 4 wherein the position determining means (150) is adapted to determine any change of position (85x,85y) of said curve (N) from one said image ($20_m$) to a subsequent image ($20_{m+1}$) and to redefine said defined image segment ($22_n$) in order that the curve (N) is maintained within the image segment ($22_n$).

6. Apparatus according to claim 4 wherein the data processing means (100) is adapted to transmit only selected data, preferably only said image segment ($22_n$) to said image analyzer module (110), thereby reducing the volume of image data being processed (100).

7. Apparatus according to claim 1, in which said light source (4) is a laser (24).

8. Apparatus according to claim 1, in which said light source (4) is a diode laser array (25).

9. Apparatus according to claim 1, comprising voltage converters (50) in order to provide high voltage levels in the internal electrical distribution cables (182) in order to reduce energy losses in said cables (182).

10. Apparatus according to claim 1, comprising exposure control means (230).

11. Apparatus according to claim 10, in which said exposure control means (230) is arranged for adjusting the intensity of the light source (4).

12. Apparatus according to claim 10, in which said exposure control means (230) is arranged for pulsing the light source (4) to give light pulses of chosen duration and interval.

13. Apparatus according to claim 1 comprising optical character recognition (OCR) means (250), for example in the form of an OCR software program module, adapted to detect codes, letters, numbers or similar in the images of the pipeline (2) in order to be able to identify individual pipe segments.

14. Apparatus according to claim 1 wherein several light sources 4a,4b,4c,4d, ... and corresponding cameras 6a,6b, 6c,6d, ... are arranged to illuminate and image around the inner periphery of the pipeline 2, in which each pair of light source and camera 4a–6a, 4b–6b, ... associated with corresponding laser sheets 5a,5b, ... are displaced longitudinally with respect to each other in the pipeline 2 in order to avoid overlapping of the fields of view 7 of the cameras and/or inspection areas along the pipe 2.

15. Apparatus according to claim 1, comprising an odometer system (200) for measuring distance and velocity for the apparatus inside a pipeline (2).

16. Apparatus according to claim 15, comprising camera line frequency adjusting means (240) using the odometer (200) output as an input.

17. Apparatus according to claim 1, comprising a mission controller (30) including switching means (32) fox turning the cameras (6) on and off, as a function of one or more of the following parameters;
programmed timers (31),
pressure (220) around the inspection device (1),
travel distance (200) inside the pipe (2),
velocity of movement (200) of the device (1) inside the pipe (2), or
accelerometer (211) readings.

18. Apparatus according to claim 1, wherein the data processing unit (100) is adapted to calculate the positions p(x) of the maxima (m) with a precision better than one pixel (sub pixel resolution) by a convolution of the light distribution along each line (M) where (m) crosses the line (N), with a chosen reference light distribution.

19. Apparatus according to claim 1, wherein the data processing unit (100) is adapted to calculate the positions p(x) of the maxima (t) with a precision better than one pixel (sub pixel resolution) by performing an integration of the light distribution along each line (M) where (M) crosses the line (N).

20. Apparatus according to claim 1, wherein the image analyzer module (110) is adapted to extract and store the intensity of the maxima (m) along a number of said lines (M) thus obtaining for each line (N) a line of grey level information i(x), where a number of stored consecutive grey level lines i(x) represents a continuous grey level image of a section of the internal wall of the pipeline (2).

21. Apparatus according to claim 20, wherein the data p(x) and i(x) are compressed in each camera using a compression algorithm prior to being stored.

22. Apparatus according to claim 21, comprising a JPEG compression algorithm.

23. Method for internal surveying of a pipeline (2) for transporting (3) a fluid comprising the steps of illuminating a line (L) of an interior surface part (9) of said pipeline (2) using a light source means (4) adapted to form one or more fan shaped beams of light (5);

registering a plurality of two-dimensional indexed images (20$_k$), said index k representing a running image number, each of said images (20) comprising intensity data for a predetermined number p of pixels in each of a predetermined number q of lines (M) of said image (20) using optical receiving means (6) positioned outside a plane formed by said fan shaped beams (5) and arranged to have in its field of view (7) the line (L) formed on the internal wall of the pipeline (2) by said fan shaped beam (5);

extracting a depth profile of said surface (9) from said recorded images (20) using a data processing unit (100) including an image analyzer module (110) with a surface depth profile analyzer module (120), said depth profile analyzer module (120) being adapted for by analyzing maxima (m) along said lines (M) for obtaining curves (N) representing said line (L) by positions p(x) of said maxima (m) for each image (20) whereby the positions p(x) of said maxima (m) in the image represents a surface profile (N);

storing said curves/surface profiles (N) in a first storage means (160.

* * * * *